United States Patent [19]

Loev

[11] 3,950,522

[45] Apr. 13, 1976

[54] PHARMACEUTICAL COMPOSITIONS AND METHODS OF INHIBITING GASTRIC ACID SECRETION

[75] Inventor: Bernard Loev, Broomall, Pa.

[73] Assignee: SmithKline Corporation, Philadelphia, Pa.

[22] Filed: Mar. 28, 1975

[21] Appl. No.: 563,411

Related U.S. Application Data

[60] Division of Ser. No. 460,315, April 12, 1974, Pat. No. 3,897,555, which is a continuation-in-part of Ser. No. 255,828, May 22, 1972, Pat. No. 3,825,547.

[52] U.S. Cl. ................ 424/248; 424/263; 424/267; 424/274

[51] Int. Cl.$^2$ ..................................... A61K 31/535
[58] Field of Search ............ 424/248, 263, 267, 274

[56] References Cited
UNITED STATES PATENTS 3,740,409   6/1973   Brenner et al. .............. 260/294.8 E

*Primary Examiner*—Frederick E. Waddell
*Attorney, Agent, or Firm*—Joan S. Keps; Richard D. Foggio; William H. Edgerton

[57] ABSTRACT

Pharmaceutical compositions and methods of inhibiting gastric acid secretion by administering N-alkenyl and N-alkynyl thioamides.

12 Claims, No Drawings

PHARMACEUTICAL COMPOSITIONS AND METHODS OF INHIBITING GASTRIC ACID SECRETION

This is a division of application Ser. No. 460,315 filed Apr. 12, 1974, now U.S. Pat. No. 3,897,555, which is a continuation-in-part of Ser. No. 255,828, filed May 22, 1972, now U.S. Pat. No. 3,825,547.

This invention relates to new N-alkenyl and N-alkynyl thioamides having pharmacological activity. In particular, these compounds inhibit gastric acid secretion.

The compounds of this invention are represented by the following formula:

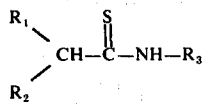

FORMULA I in which:
$R_1$ is 2-pyridyl, 2-pyrimidyl, 4-pyrimidyl, 2-pyrazinyl, 2-pyrrolyl, 2-quinolyl, 2-thiazolyl or 4-thiazolyl;
$R_2$ is hydrogen, lower alkyl, lower alkenyl, lower alkoxy, allyloxy, cyclopropanemethoxy, phenyl, benzyl or $-(CH_2)_n-NR_4R_5$;
$R_3$ is an allyl or propargyl group optionally substituted by methyl or ethyl groups, said $R_3$ having 3-6 carbon atoms;
$R_4$ and $R_5$ are lower alkyl or taken together with the nitrogen atom to which they are attached form a piperidino, pyrrolidino, morpholino or N-lower alkyl-piperazino ring and
$n$ is 0 or 1.

This invention also includes pharmaceutically acceptable acid addition salts of the compounds of Formula I.

The pharmacologically active compounds of this invention have the basic structure of Formula I. However, it is apparent to one skilled in the art that well known nuclear substituents such as lower alkyl, lower alkoxy or halogen may be incorporated on the phenyl and heterocyclic rings. These substituted compounds are used as are the parent compounds.

Preferred compounds of this invention are represented by Formula I in which $R_2$ is hydrogen, lower alkyl or $-CH_2-NR_4R_5$; $R_3$ is allyl optionally substituted by methyl or ethyl, said $R_3$ having 3-6 carbon atoms and $R_4$ and $R_5$ are methyl or ethyl or taken together with the nitrogen atom to which they are attached form a piperidino, pyrrolidino or morpholino ring.

Advantageous compounds of this invention are represented by Formula I in which $R_1$ is 2-pyridyl, $R_2$ is hydrogen, lower alkyl or morpholinomethyl and $R_3$ is allyl.

Most preferably, in the compounds of Formula I, $R_1$ is 2-pyridyl.

Particularly advantageous compounds of this invention are N-allyl-2-(2-pyridyl)thioacetamide and N-allyl-3-morpholino-2-(2-pyridyl)thiopropionamide.

The compounds of this invention product inhibition of gastric acid secretion. This activity is demonstrated by administration to pylorus ligated rats at doses of about 2.0 mg./kg. to about 50 mg./kg. orally. In this procedure, compounds which produce an increase in gastric pH or a decrease in the volume of gastric juice or both are considered active.

The compounds of this invention are prepared by the following procedures:

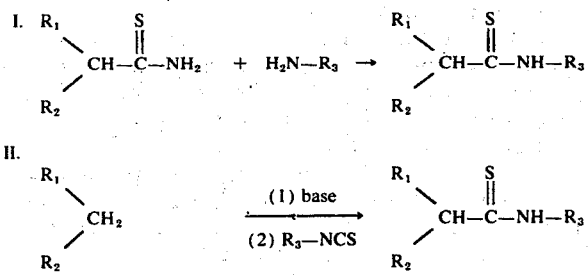

According to procedure I, a substituted thioacetamide is reacted with an alkenylamine or alkynylamine to give the N-alkenyl and N-alkynyl thioamides of this invention. The reaction may be run at −20°C. to 100°C. but is preferably carried out at about 0°C. to 5°C. The reaction may be run in aqueous or non-aqueous systems. Excess of the amine may be used as solvent. The use of an aqueous system is preferred.

According to procedure II, a methyl (or substituted methyl) heterocycle is reacted with strong base such as phenyl or butyl lithium and then with an alkenyl or alkynyl isothiocyanate to give the N-alkenyl and N-alkynyl thioamides.

The compounds of Formula I in which $R_2$ is $-CH_2-NR_4R_5$ may be prepared by reacting the compounds of Formula I in which $R_2$ is hydrogen with formaldehyde and the appropriate amine.

The pharmaceutically acceptable acid addition salts of the compounds of Formula I are formed with organic and inorganic acids by methods known to the art. For example, the base is reacted with an organic or inorganic acid in aqueous miscible solvent, such as acetone or ethanol, with isolation of the salt by concentration and cooling or in aqueous immiscible solvent, such as ethyl ether or chloroform, with the desired salt separated directly. Exemplary of the salts which are included in this invention are maleate, fumarate, succinate, oxalate, benzoate, methanesulfonate, ethanedisulfonate, benzenesulfonate, acetate, propionate, tartrate, citrate, hydrochloride, hydrobromide, sulfate, sulfamate, phosphate and nitrate salts.

The compounds of this invention are administered internally either parenterally, rectally or, preferably, orally in an amount to produce the desired biological activity.

Preferably, the compounds are administered in conventional dosage forms prepared by combining an appropriate dose of the compound with standard pharmaceutical carriers.

Pharmaceutical compositions having gastric acid secretion inhibitory activity, in dosage unit form, comprising a pharmaceutical carrier and a gastric acid secretion inhibiting amount of a compound of Formula I or a pharmaceutically acceptable acid addition salt thereof are objects of this invention.

The pharmaceutical carrier may be for example a solid of a liquid. Exemplary of solid carriers are lactose, magnesium stearate, terra alba, sucrose, talc, stearic acid, gelatin, agar, pectin, acacia or cocoa butter. The amount of solid carrier will vary widely but preferably will be from about 25 mg. to about 1 gm. Exemplary of liquid carriers are syrup, peanut oil, olive oil, sesame oil, propylene glycol, polyethylene glycol (mol. wt. 200–400) and water. The carrier or diluent may include a time delay material well known to the art such as, for example, glyceryl monostearate or glyceryl distearate alone or with a wax.

A wide variety or pharmaceutical forms can be employed, for example the preparation may take the form of tablets, capsules, powders, suppositories, troches, lozenges, syrups, emulsions, sterile injectable liquids or liquid suspensions or solutions.

The pharmaceutical compositions are prepared by conventional techniques involving procedures such as mixing, granulating and compressing or dissolving the ingredients as appropriate to the desired preparation.

The methods of inhibiting gastric acid secretion in accordance with this invention comprise administering internally to an animal an effective amount of a compound of Formula I or a pharmaceutically acceptable acid addition salt thereof. The active ingredients will preferably be administered in dosage unit form as described above.

The compounds of this invention will be administered in a daily dosage regimen of from about 10 mg. to about 2 g., preferably from about 25 mg. to about 1 g. Advantageously, equal doses will be administered 1 to 4 times per day. Dosage units will contain from about 10 mg. to about 500 mg., preferably from about 25 mg. to about 250 mg., of the active ingredient.

When administration is carried out as described above, gastric acid secretion is inhibited.

One skilled in the art will recognize that in determining the amounts of the active ingredients in the claimed compositions and used in the claimed methods, the activity of the chemical ingredient as well as the size of the host animal must be considered.

The terms "lower alkyl" and "lower alkoxy" where used herein denote groups having, preferably, 1–4 carbon atoms; "lower alkenyl" denotes groups having, preferably 2–4 carbon atoms and "halogen" denotes chloro, bromo or fluoro.

The following examples are not limiting but are illustrative of the invention.

EXAMPLE 1

A solution of 9.3 g. (0.1 mole) of 2-picoline in 50 ml. of anhydrous ether is added dropwise at 15°C. to 50 ml. of a 2.1M solution of phenyl lithium in benzene/ether under nitrogen. The resulting mixture is stirred for 1 hour, then added dropwise to a stirred solution of 9.9 g. (0.1 mole) of allyl isothiocyanate in 200 ml. of anhydrous ether at −50°C. under nitrogen. The mixture is stirred for 15 minutes after the addition is complete and then poured into 150 ml. of dilute hydrochloric acid/ice and stirred. The layers are separated and the aqueous phase is basified with 5% aqueous sodium carbonate solution and then extracted with ethyl acetate. The extracts are dried and concentrated and the residue is recrystallized from benzene/petroleum ether to give N-allyl-2-(2-pyridyl)thioacetamide, m.p. 67°–68°C.

EXAMPLE 2

To 4.0 g. (0.026 mole) of 2-(2-pyridyl)thioacetamide in 20 ml. of water at 0°C. is added 2.9 g. (0.053 mole) of propargylamine with stirring and the resulting suspension is allowed to stand overnight at 5°C. Ethanol (5 ml.) is added and the mixture is stirred for 5 hours, then extracted with dichloromethane. The extracts are dried and concentrated. The residue is chromatographed on a silica gel "dry-column", using 1:10 ethyl acetate/ether as the eluant. The product fraction is treated with charcoal, filtered, concentrated and the residue is recrystallized from benzene/ligroin to give N-propargyl-2-(2-pyridyl)thioacetamide, m.p. 62°–63°C.

EXAMPLE 3

A solution of 5.0 g. (0.026 mole) of N-allyl-2-(2-pyridyl)thioacetamide in 80 ml. of methanol is treated at 25°C. with 3.4 g. (0.039 mole) of morpholine and 1.17 g. (0.039 mole) of formaldehyde and the mixture is stirred for 24 hours.

The solvent is evaporated at 25°C. and the resulting oil is triturated with petroleum ether until crystallization is complete. Recrystallization from ether gives N-allyl-3-morpholino-2-(2-pyridyl)thiopropionamide, m.p. 84°–86°C.

EXAMPLE 4

A solution of 9.95 g. (0.081 mole) of 2-(methoxymethyl)pyridine in 80 ml. of dry benzene is added dropwise to a chilled solution of 40 ml. (0.084 mole) of phenyl lithium in 80 ml. of dry benzene. The mixture is stirred at 0°C. for 1 hour after the addition is complete. Then 8.02 g. of allyl isothiocyanate in 50 ml. of benzene is added dropwise and the mixture is allowed to come to room temperature gradually. The mixture is then diluted with 500 ml. of water and acidified with 10% hydrochloric fractions The layers are separated and the organic layer is washed several times with water. The aqueous layers are combined, neutralized with 10% aqueous sodium hydroxide solution and then brought to pH 9 5% aqueous sodium bicarbonate solution, then extracted with chloroform. The chloroform extracts are washed once with brine and dried over magnesium sulfate. The solvent is removed and the residue is chromatographed on a silica gel column, eluting with ethyl acetate. The fraction, containing the product are combined and evaporated and the residue is recrystallized from ethyl acetate/hexane to give N-allyl-2-methoxy-2-(2-pyridyl)thioacetamide, m.p. 59.5°–60°C.

EXAMPLE 5

By the procedure of Example 1, using in place of 2-picoline, the following compounds:
2-ethylpyridine
2-propylpyridine
2-isobutylpyridine
2-n-butylpyridine
2-benzylpyridine
2-methylpyrazine
2-methylpyrimidine
4-methylpyrimidine 2-methylpyrrole
2-methylquinoline
2-ethylquinoline
2-methylthiazole
2-ethylthiazole
2-benzylthiazole
4-methylthiazole the products are, respectively:
N-allyl-2-(2-pyridyl)thiopropanamide
N-allyl-2-(2-pyridyl)thiobutanamide
N-allyl-3-methyl-2-(2-pyridyl)thiobutanamide
N-allyl-2-(2-pyridyl)thiopentanamide
N-allyl-2-phenyl-2-(2-pyridyl)thioacetamide
N-allyl-2-(2-pyrazinyl)thioacetamide
N-allyl-2-(2-pyrimidyl)thioacetamide
N-allyl-2-(4-pyrimidyl)thioacetamide
N-allyl-2-(2-pyrrolyl)thioacetamide
N-allyl-2-(2-quinolyl)thioacetamide
N-ally-2-(2-quinolyl)thiopropanamide
N-allyl-2-(2-thiazolyl)thioacetamide
N-allyl-2-(2-thiazolyl)thiopropanamide
N-allyl-2-phenyl-2-(2-thiazolyl)thioacetamide
N-allyl-2-(4-thioazolyl)thioacetamide

EXAMPLE 6

Using 2-[2-(dimethylamino)ethyl]pyridine in place of 2-picoline in the procedure of Example 1, the product is N-allyl-3-dimethylamino-2-(2-pyridyl)thiopropanamide.

By the same procedure, using 2-(dimethylaminomethyl)pyrrole, the product is N-allyl-2-dimethylamino-2-(2-pyrrolyl)thioacetamide.

EXAMPLE 7

Alternatively, N-allyl-2-(2-pyridyl)thioacetamide is prepared by the following procedure.

Allylamine (3.1 g.) is added with stirring to 4.0 g. of 2-(2-pyridyl)thioacetamide in 20 ml. of water at 0°C. The resulting mixture is allowed to stand overnight at 5°C., then 5 ml. of ethanol is added. The mixture is stirred for 5 hours and then extracted with dichloromethane. The extracts are dried and concentrated and the residue is chromatographed on a silica gel "drycolumn" to give N-allyl-2-(2-pyridyl)thioacetamide.

EXAMPLE 8

By the procedure of Example 7, reacting 2-(2-pyridyl)-4-thiopentenamide with allylamine gives N-allyl-2-(2-pyridyl)-4-thiopentenamide.

EXAMPLE 9

To cold 2-pyridinecarboxaldehyde (21.4 g., 0.2 mole) is added dimethylamine (22.5 g. of a 40% aqueous solution, 0.2 mole) and the solution is neutralized with concentrated hydrochloric acid. To the stirred neutralized solution is added 14.4 g. (0.22 mole) of potassium cyanide. The mixture is stirred overnight, then diluted with water, transferred to a separatory funnel and repeatedly extracted with chloroform. The combined chloroform extracts are washed 3 times with water, once with brine and dried over magnesium sulfate. The mixture is filtered, the solvent is removed under reduced pressure and methanol is added to the residue. The mixture is allowed to stand at −20°C. for 18 hours, then filtered. The filtrate is concentrated and distilled in vacuo to give 2-dimethylamino-2-(2-pyridyl)acetonitrile.

2-Dimethylamino-2-(2-pyridyl)acetonitrile (11.4 g., 0.07 m.) is dissolved in 200 ml. of dry pyridine containing 5 ml. of anhydrous triethylamine. Hydrogen sulfide is bubbled into the stirred solution for 7 hours and the solution is then stirred for 17 hours. This procedure is repeated for 5 days. Then the mixture is stirred for an additional 48 hours. The solvent is then removed under reduced pressure and the residue is recrystallized from ethanol to give 2-dimethylamino-2-(2-pyridyl)thioacetamide.

2-Dimethylamino-2-(2-pyridyl)thioacetamide is reacted with allylamine by the procedure of Example 7 to give N-allyl-2-dimethylamino-2-(2-pyridyl)thioacetamide.

By the same procedure, using the following substituted acetonitriles:
2-diethylamino-2-(2-pyridyl)acetonitrile
2-pyrrolidino-2-(2-pyridyl)acetonitrile
2-piperidino-2-(2-pyridyl)acetonitrile
2-dimethylamino-2-(2-quinolyl)acetonitrile
2-piperidino-2-(2-quinolyl)acetonitrile the products are, respectively:
N-allyl-2-diethylamino-2-(2-pyridyl)thioacetamide
N-allyl-2-pyrrolidino-2-(2-pyridyl)thioacetamide
N-allyl-2-piperidino-2-(2-pyridyl)thioacetamide
N-allyl-2-dimethylamino-2-(2-quinolyl)thioacetamide
N-allyl-2-piperidino-2-(2-quinolyl)thioacetamide.

Also, by the same procedure, using a N-lower alkylpiperazine in place of dimethylamine, the N-allyl-2-(4-lower alkylpiperazino)-2-(2-pyridyl)thioacetamides, such as the 4-methylpiperazino and 4-ethylpiperazino compounds, are obtained.

Similarly, using morpholine in place of dimethylamine, the product is N-allyl-2-morpholino-2-(2-pyridyl)thioacetamide.

EXAMPLE 10

By the procedure of Example 3, using in place of morpholine, the following compounds:
diethylamine
dipropylamine
dibutylamine
pyrrolidine
piperidine
N-methylpiperazine
N-ethylpiperazine
N-propylpiperazine
N-butylpiperazine the products are, respectively:
N-allyl-3-diethylamino-2-(2-pyridyl)thiopropanamide
N-allyl-3-dipropylamino-2-(2-pyridyl)thiopropanamide
N-allyl-3-butylamino-2-(2-pyridyl)thiopropanamide
N-allyl-3-pyrrolidino-2-(2-pyridyl)thiopropanamide
N-allyl-3-piperidino-2-(2-pyridyl)thiopropanamide
N-allyl-3-(4-methylpiperazino)-2-(2-pyridyl)thiopropanamide
N-allyl-3-(4-ethylpiperazino)-2-(2-pyridyl)thiopropanamide
N-allyl-3-(4-propylpiperazino)-2-(2-pyridyl)thiopropanamide
N-allyl-3-(4-butylpiperazino)-2-(2-pyridyl)thiopropanamide.

EXAMPLE 11

By the procedure of Example 7, 2-benzyl-2-(2-pyridyl)thioacetamide is reacted with allylamine to give N-allyl-2-benzyl-2-(2-pyridyl)thioacetamide.

EXAMPLE 12

By the procedure of Example 2, using the following thioamides in place of 2-(2-pyridyl)thioacetamide:
- 3-methyl-2-(2-pyridyl)thiobutanamide
- 2-phenyl-2-(2-pyridyl)thioacetamide
- 2-(2-pyridyl)thiopropanamide
- 2-(2-pyridyl)thiobutanamide
- 2-(2-pyridyl)thiopentanamide
- 2-(2-pyridyl)thiohexanamide
- 2-(2-pyridyl)-4-thiopentenamide
- 2-(4-chlorophenyl)-2-(2-pyridyl)thioacetamide
- 2-benzyl-2-(2-pyridyl)thioacetamide the products are, respectively:
- 3-methyl-N-propargyl-2-(2-pyridyl)thiobutanamide
- 2-phenyl-N-propargyl-2-(2-pyridyl)thioacetamide
- N-propargyl-2-(2-pyridyl)thiopropanamide
- N-propargyl-2-(2-pyridyl)thiobutanamide
- N-propargyl-2-(2-pyridyl)thiopentanamide
- N-propargyl-2-(2-pyridyl)thiohexanamide
- N-propargyl-2-(2-pyridyl)-4-thiopentenamide
- 2-(4-chlorophenyl)-N-propargyl-2-(2-pyridyl)thioacetamide
- 2-benzyl-N-propargyl-2-(2-pyridyl)thioacetamide.

EXAMPLE 13

By the procedure of Example 7, using in place of allylamine, the following amines:
- 2-ethylallylamine
- 1-methylallylamine
- 2-methylallylamine
- 2-butenylamine
- 4-methyl-2-pentenylamine
- 1-ethyl-1-methyl-2-propynylamine
- 2-butynylamine
- 2-pentynylamine the products are, respectively:
- N-(2-ethylallyl)-2-(2-pyridyl)thioacetamide
- N-(1-methylallyl)-2-(2-pyridyl)thioacetamide
- N-(2-methylallyl)-2-(2-pyridyl)thioacetamide
- N-(2-butenyl)-2-(2-pyridyl)thioacetamide
- N-(4-methyl-2-pentenyl)-2-(2-pyridyl)thioacetamide
- N-(1-ethyl-1-methyl-2-propynyl)-2-(2-pyridyl)thioacetamide
- N-(2-butynyl)-2-(2-pyridyl)thioacetamide
- N-(2-pentynyl)-2-(2-pyridyl)thioacetamide.

EXAMPLE 14

2-(Chloromethyl)pyridine hydrochloride (16.3 g., 0.1 mole) is dissolved in 100 ml. of methanol. Sodium ethoxide (0.22 mole of sodium dissolved in 150 ml. of ethanol) is added dropwise. The resulting mixture is heated at reflux for 18 hours, then filtered. The filtrate is concentrated. Water and ether are added, the aqueous phase is extracted with ether and the combined ethereal phases are washed with water and saturated aqueous sodium chloride, then dried over magnesium sulfate, concentrated and distilled to give 2-(ethoxymethyl)pyridine.

By the procedure of Example 4, using 2-(ethoxymethyl)pyridine in place of 2-(methoxymethyl)pyridine, the product is N-allyl-2-ethoxy-2-(2-pyridyl)thioacetamide.

Similarly, using in place of sodium ethoxide, the following sodium alkoxides:
- sodium propoxide
- sodium butoxide
- sodium allyloxide
- sodium cyclopropanemethoxide the products are, respectively:
- N-allyl-2-propoxy-2-(2-pyridyl)thioacetamide
- N-allyl-2-butoxy-2-(2-pyridyl)thioacetamide
- N-allyl-2-allyloxy-2-(2-pyridyl)thioacetamide
- N-allyl-2-cyclopropanemethoxy-2-(2-pyridyl)thioacetamide.

EXAMPLE 15

2-(6-Methyl-2-pyridyl)-3-butenenitrile [prepared by treating α-(6-methyl-2-pyridyl)-2-propenol with thionyl chloride and reacting the resulting 2-(1-chloro-2-propenyl)-6-methylpyridine with sodium cyanide] is treated with hydrogen sulfide by the procedure described in Example 9, to give 2-(6-methyl-2-pyridyl)-3-thiobutenamide.

Reacting 2-(6-methyl-2-pyridyl)-3-thiobutenamide with allylamine by the procedure of Example 7 gives N-allyl-2-(6-methyl-2-pyridyl)-3-thiobutenamide.

EXAMPLE 16

A solution of 5.9 g. of 2-pyridylacetonitrile in 15 ml. of dimethylsulfoxide is added to a suspension of 1.2 g. of sodium hydride in 25 ml. of dimethylsulfoxide with stirring. The mixture is heated on a stream bath for 2 hours, then cooled to room temperature. 1-Chloro-2-butene (4.5 g.) is added dropwise with stirring. The mixture is heated on a steam bath, with stirring, for 10 hours, then most of the solvent is removed in vacuo. Water is added to the residue, then 100 ml. of ether is added. The ethereal solution is separated from the aqueous layer and rinsed several times with water, then dried, concentrated and distilled to give 2-(2-pyridyl)-4-hexenenitrile.

The above prepared nitrile is treated with hydrogen sulfide by the procedure of Example 9 to give 2-(2-pyridyl)-4-thiohexenamide.

Reacting 2-(2-pyridyl)-4-thiohexenamide with allylamine by the procedure of Example 7 gives N-allyl-2-(2-pyridyl)-4-thiohexenamide.

EXAMPLE 17

N-Allyl-2-(2-pyridyl)thioacetamide (500 mg.) in ether is treated with ethereal hydrogen chloride and the resulting precipitate is filtered off to give N-allyl-2-(2-pyridyl)thioacetamide hydrochloride.

Similarly, treating N-propargyl-2-(2-pyridyl)thioacetamide with ethereal hydrogen chloride gives N-propargyl-2-(2-pyridyl)thioacetamide hydrochloride and treating N-allyl-3-morpholino-2-(2-pyridyl)thiopropionamide with ethereal hydrogen chloride gives N-allyl-3-morpholino-2-(2-pyridyl)thiopropionamide dihydrochloride.

In the same manner, using ethereal hydrogen bromide, the hydrobromide salts are prepared.

EXAMPLE 18

Treating N-allyl-2-(2-pyridyl)thioacetamide with an equimolar amount of maleic acid in ethanol, then removing the solvent under reduced pressure gives N-allyl-2-(2-pyridyl)thioacetamide maleate.

Similarly, using citric acid, N-allyl-2-(2-pyridyl)thioacetamide citrate is prepared.

EXAMPLE 19

| Ingredients | Amounts |
|---|---|
| N-Allyl-2-(2-pyridyl)thioacetamide | 75 mg. |
| Lactose | 100 mg. |
| Magnesium stearate | 5 mg. |

The ingredients are mixed and filled into a hard gelatin capsule.

EXAMPLE 20

| Ingredients | Amounts |
|---|---|
| N-Allyl-3-morpholino-2-(2-pyridyl)thiopropionamide | 100 mg. |
| Calcium sulfate dihydrate | 125 mg. |
| Sucrose | 25 mg. |
| Starch | 15 mg. |
| Talc | 5 mg. |
| Stearic acid | 3 mg. |

The sucrose, calcium sulfate dihydrate and N-allyl-3-morpholino-2-(2-pyridyl)thiopropionamide are thoroughly mixed and granulated with 10% gelatin solution. The wet granules are screened, dried and then mixed with the starch, talc and stearic acid, screened and compressed into a tablet.

The compositions prepared as in Examples 19 and 20 are administered orally to a subject having excessive gastric acid secretion within the dose ranges given hereabove.

What is claimed is:

1. A pharmaceutical composition having gastric acid secretion inhibitory activity, in dosage unit form, comprising a pharmaceutical carrier and a gastric acid secretion inhibiting amount of a thioamide compound of the formula:

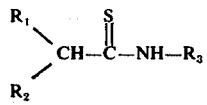

in which:
$R_1$ is 2-pyridyl;
$R_2$ is $-(CH_2)_n-NR_4R_5$;
$R_3$ is an allyl or propargyl group optionally substituted by methyl or ethyl groups, said $R_3$ having 3–6 carbon atoms;
$R_4$ and $R_5$ are lower alkyl or taken together with the nitrogen atom to which they are attached form a piperidino, pyrrolidino, morpholino or N-lower alkyl-piperazino ring and
$n$ is 0 or 1
or a pharmaceutically acceptable acid addition salt thereof.

2. The pharmaceutical composition of claim 1 in which $R_2$ is $-(CH_2)_n-NR_4R_5$, $R_3$ is allyl optionally substituted by methyl or ethyl, said $R_3$ having 3–6 carbon atoms and $R_4$ and $R_5$ are methyl or ethyl or taken together with the nitrogen atom to which they are attached form a piperidino, pyrrolidino or morpholino ring.

3. The pharmaceutical composition of claim 1 in which $R_2$ is morpholinomethyl and $R_3$ is allyl.

4. The pharmaceutical composition of claim 1 in which the thioamide compound is N-allyl-3-morpholino-2-(2-pyridyl)thiopropionamide.

5. The pharmaceutical composition of claim 1 in which the thioamide compound is present in an amount of from about 10 mg. to about 500 mg.

6. The pharmaceutical composition of claim 1 in which the thioamide compound is N-allyl-3-dimethylamino-2-(2-pyridyl)thiopropanamide.

7. The pharmaceutical composition of claim 1 in which the thioamide compound is N-allyl-2-dimethylamino-2-(2-pyridyl)thioacetamide.

8. A method of inhibiting gastric acid secretion in an animal in need of said treatment which comprises administering internally to said animal an effective gastric acid inhibiting amount of a thioamide compound of the formula:

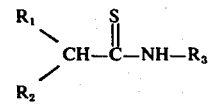

in which:
$R_1$ is 2-pyridyl;
$R_2$ is $-(CH_2)_n-NR_4R_5$;
$R_3$ is an allyl or propargyl group optionally substituted by methyl or ethyl groups, said $R_3$ having 3–6 carbon atoms;
$R_4$ and $R_5$ are lower alkyl or taken together with the nitrogen atom to which they are attached form a piperidino, pyrrolidino, morpholino or N-lower alkylpiperazino ring and
$n$ is 0 or 1
or a pharmaceutically acceptable acid addition salt thereof.

9. The method of claim 8 in which the thioamide compound is N-allyl-3-morpholino-2-(2-pyridyl)thiopropionamide.

10. The method of claim 8 in which the thioamide compound is administered in a daily doasge of from about 10 mg. to about 2 g.

11. The method of claim 8 in which the thioamide compound is N-allyl-3-dimethylamino-2-(2-pyridyl)-thiopropanamide.

12. The method of claim 8 in which the thioamide compound is N-allyl-2-dimethylamino-2-(2-pyridyl)-thioacetamide.

* * * * *

UNITED STATES PATENT AND TRADEMARK OFFICE
CERTIFICATE OF CORRECTION

PATENT NO. : 3,950,522
DATED : April 13, 1976
INVENTOR(S) : Bernard Loev

It is certified that error appears in the above-identified patent and that said Letters Patent are hereby corrected as shown below:

Column 3, line 8, "of a" should read -- or a -- .

Column 4, line 43, "fractions" should read -- acid. -- .

Column 4, line 52, "fraction," should read -- fractions -- .

Column 6, line 58, "-3-butylamino" should read -- -3-dibutylamino -- .

Signed and Sealed this

Thirteenth Day of July 1976

[SEAL]

Attest:

RUTH C. MASON
Attesting Officer

C. MARSHALL DANN
Commissioner of Patents and Trademarks